United States Patent [19]

Edwards

[11] 4,285,973

[45] Aug. 25, 1981

[54] LIQUID COMPOSITION FOR APPLICATION TO THE SKIN

[75] Inventor: Diane B. Edwards, Carol Stream, Ill.

[73] Assignee: Alberto-Culver Company, Melrose Park, Ill.

[21] Appl. No.: 59,441

[22] Filed: Jul. 20, 1979

[51] Int. Cl.$^3$ .............................................. A61K 7/48
[52] U.S. Cl. ................................. 424/358; 424/361; 424/362; 424/365
[58] Field of Search .................... 424/358, 168, 362

[56] References Cited

U.S. PATENT DOCUMENTS

| | | | |
|---|---|---|---|
| 2,266,992 | 12/1941 | Roblin, Jr. ...................... 424/366 X |
| 3,981,990 | 9/1976 | Kelly et al. .......................... 424/168 |
| 4,005,193 | 1/1977 | Green et al. ......................... 424/168 |
| 4,115,548 | 9/1978 | Marsh et al. ......................... 424/168 |
| 4,172,887 | 10/1979 | Vanderberghe ...................... 424/70 |

FOREIGN PATENT DOCUMENTS

| | | | |
|---|---|---|---|
| 920162 | 1/1964 | France .................................... 424/358 |
| 2371919 | 6/1978 | France .................................... 424/365 |
| 46-14353 | 4/1971 | Japan ..................................... 424/358 |
| 46-35760 | 10/1971 | Japan ..................................... 424/361 |
| 48-1504 | 1/1973 | Japan ..................................... 424/361 |
| 48-1505 | 1/1973 | Japan ..................................... 424/365 |

OTHER PUBLICATIONS

Research Disclosure, 3/1975, No. 131.

*Primary Examiner*—Dale R. Ore

[57] ABSTRACT

A protective skin lotion comprises a liquid composition in the form of an oil-in-water emulsion in which the oil phase is composed of cosmetic emollient oils, and in which the water phase contains quaternary ammonium cellulose ether polymer. The formulation improvement comprises incorporating a lactate salt in the water phase of the lotion, and preferably, also, a quaternary ammonium salt in the oil phase. The retention of the lotion on the skin is improved by the presence of the lactate salt, and to an even greater extent by the use of both the lactate salt and the quaternary ammonium salt.

5 Claims, No Drawings

LIQUID COMPOSITION FOR APPLICATION TO THE SKIN

BACKGROUND AND PRIOR ART

Skin lotions are well known in the cosmetic arts and are widely used which are composed of oil-in-water emulsions of emollient oils. It is also known that the incorporation of quaternary ammonium cellulose ether polymers in the water phase of such lotions tends to protect the skin against irritants and allergens, including anionic synthetic detergents (e.g. sodium lauryl sulfate), thioglycollate depilatories, and ordinary soap. See Faucher et al Cosmetics and Toiletries, 92, 39–44 (June, 1977); and "Polymer JR for Skin Care", Union Carbide Corporation (1977). The cationic cellulose ether polymers are prepared as described in United States patent 3,472,840, and a representative commercially available polymer is Polymer JR 400 (Union Carbide Corp., New York, N.Y.), which has a molecular weight of approximately 400,000. Such quaternary ammonium cellulose ethers exhibit a degree of substantivity to the skin. It has been proposed that the cationic cellulose polymers exert an effect upon the *stratum corneum*, and that this effect may be the prevention of loss of barrier function. However, the exact mechanism by which the cationic cellulose polymers exert their protective action is not known with certainty.

Lactate salts such as sodium lactate have been studied as ingredients of skin creams and cosmetic preparations. They may provide a buffering action in the cosmetic preparation, and also provide a humectant or skin moisturizing action. See Middleton, Cosmetics and Toiletries, 92, 34–38 (May, 1977); and Osipow, Drug and Cosmetic Industry, 88, 438 (April, 1961). Quaternary ammonium lactates as ingredients of topical preparations such as for the treatment of acne are disclosed in U.S. Pat. No. 4,021,572. According to the disclosure of that patent, quaternary ammonium lactates penetrate the skin better than ordinary lactate salts, such as sodium lactate.

SUMMARY OF INVENTION

This invention is based in part on the discovery that the substantivity or retention of quaternary ammonium cellulose ether polymers on the skin can be substantially improved where the polymer-containing water phase of the skin lotion also contains lactate salt. In connection with the development of the present invention, it was further discovered that if the composition, preferably the oil phase, contains a quaternary ammonium salt in the standard chloride or sulfate form that the substantivity or retention of the cellulose polymer is further improved. However, if the quaternary ammonium salt is present alone (without the lactate salt) the substantivity or retention of the cellulose polymer is decreased. It is quite surprising that the quaternary salt in the oil phase acts synergistically with the lactate salt in the water phase to promote retention of the cellulose polymer. There is apparently an interaction between the lactate and the quaternary, either when the composition is formed or when it is applied. Therefore, in a preferred embodiment of the present invention, the oil-in-water emulsion should contain three interacting ingredients: the cationic cellulose polymer, the lactate salt, and the quaternary ammonium salt.

DETAILED DESCRIPTION

The present invention can be practiced with skin lotions comprising oil-in-water emulsions where the oil phase comprises primarily a mixture of cosmetic emollient oils. In general, these are water-immiscible oily liquids which are acceptable in cosmetic preparations such as skin lotions and creams. These include the mineral or hydrocarbon oils, the oily alcohol such as cetyl alcohol, fatty acid derivatives, such as isopropyl palmitate or myristate, and glyceryl monostearate, silicone oils such as dimethicone, lanolin derivatives such as lanolin alcohol, and the like. Such emollient oils are generally used in various admixtures, and for the purpose of the present invention there is nothing critical about any particular mixture of emollient oils. Further, the proportions of the oil-in-water phases may be varied over a considerable range, although the oil phase will usually be the minor phase in terms of weight or volume. For example, the liquid compositions may contain from 5 to 35% by weight of an admixture of the emollient oils as the internal or dispersed phase with the external or continuous water phase comprising from 95 to 65% by weight of the composition. For commercial purposes, the emollient oils may advantageously comprise from about 8 to 20% by weight of the composition such as, for example, 12 to 15%.

The quaternary ammonium cellulose ether polymer for incorporation in the water phase may be prepared as described in U.S. Pat. No. 3,472,840 or obtained from a commercial source. For example, the Polymer JR products of Union Carbide Corporation, New York, N.Y. can be used, such as Polymer JR 400. Also available from the same source is Polymer JR 125 and Polymer JR 30M. In general, this invention can be practiced with any cationic cellulose polymer in the water phase. For example, the water phase may contain from 0.05 to 3.0% of the cellulose polymer based on the weight of the total composition. In preferred embodiments, the cellulose polymer may be present in an amount of from 0.1 to 0.5% on the same basis, such as about 0.3%. The quaternary ammonium groups of the polymer may be in the chloride or sulfate salt form, for example, and will not usually be in the form of their lactate salts.

In accordance with the present invention, a lactate salt is incorporated in the emulsion preparation in the amount of from 0.3 to 3.0% by weight based on the total composition. The lactate salt may conveniently be sodium lactate, but other lactate salts can be used such as potassium lactate or ammonium lactate. In preferred embodiments, the liquid compositions will contain from about 0.5 to 1.5% of the lactate salt such as about 0.8 to 0.9%. Although the lactate salt may be used alone to improve the retention of the cellulose polymer, it is preferred to employ it in conjunction with an oil-soluble quaternary ammonium salt such as dimethyl di-(hydrogenated tallow) quaternary ammonium chloride.

More generally, dimethyl di-aliphatic quaternary ammonium salts can be employed such as those containing from 12 to 18 carbons in the aliphatic groups. Where the aliphatic groups are provided by hydrogenated tallow, they will be composed predominantly of stearyl and palmityl groups. Instead of the two aliphatic groups, the quaternary ammonium salt may contain an aromatic group such as a benzyl group. For example, dimethyl benzyl quaternary ammonium chloride can be used. Quaternaries may be used in their commonly available salt forms, such as the chloride or sulfate salts.

Such quaternaries are usually not available as their lactate salts. The quaternary salt may be present in an amount of from 0.5 to 4.0% based on the weight of the total composition, preferably in an amount of from about 1.0 to 3.0%, and are preferably dispersed in the emollient oil phase. Alternatively, the oil-soluble quaternary may be initially dispersed in the water phase and transferred therefrom to the oil phase.

It is preferred that the water phase of the liquid compositions have a slightly acid pH, such as a pH from about 5.0 to 6.0. The lactate salt will provide a buffering action, and it has been found that the pH of the complete preparation remains stable within the desired pH range. Where required, minor pH adjustments can be made with standard reagents.

A preferred formula for liquid compositions prepared in accordance with the present invention is set out below.

| Preferred Formula | |
|---|---|
| Ingredients | Weight % |
| Emollient oil | 8–20 |
| Quaternary ammonium cellulose ether polymer | 0.1–0.5 |
| Lactate salt | 0.5–1.5 |
| Quaternary ammonium salt | 1.0–3.0 |
| Water | q.s. |

In the foregoing formula, for example, the emollient oil may comprise the following mixture.

| Emollient Oil Mixture | |
|---|---|
| Oils and Emulsifier | Parts by Weight |
| Cetyl alcohol | 4.0 |
| Mineral oil | 4.0 |
| Isopropyl palmitate | 3.0 |
| Dimethicone | 1.0 |
| Lanolin alcohol | 0.5 |
| Glyceryl monostearate | 1.0 |

It will be understood that other ingredients may be included to provide a cosmetically elegant product, such as preservatives, coloring agents, perfume, etc. If desired, water-soluble emollient agents may be incorporated in the water phase. For example, from 1.0 to 5.0% of propylene glycol may be incorporated in the water phase, but such ingredients should be considered optional, although they may provide desirable emollient or humectant properties.

In preparing preparations in accordance with the present invention, the oil-in-water phases will be prepared separately. For example, the water phase ingredients may be dissolved in heated water, such as water at about 150°–170° F. As indicated above, these ingredients will include the cellulose polymer, the lactate salt, and other water-soluble ingredients if present, such as propylene glycol.

The oil phase is prepared from a mixture of the emollient oils by heating the oils together, such as at a temperature of about 150° to 170° F., to form a homogeneous mixture. The other oil-phase ingredients may be incorporated by dissolving or dispersing therein, such as the quaternary ammonium salt, an oil-soluble emulsifier, etc.

After the two phases have been separately prepared, they are combined in the desired proportions by pumping the water phase into the oil phase. It will be understood that the ingredients should include an emulsifier promoting the formation of an oil-in-water emulsion. For example, the emulsifier may comprise glyceryl monostearate or other component of the emollient oil phase having emulsifying properties. For example, as little as 1.0% by weight of glyceryl monostearate will provide the desired emulsifying action. A whitener such as titanium dioxide may be stirred into the emulsion thus formed, and the emulsion cooled, for example, to a temperature of about 130° F. before adding the lactate salt, which is dissolved in the aqueous phase of the emulsion. The emulsion may then be further cooled, such as to a temperature of 100° F. before adding any highly volatile ingredients such as perfume.

As indicated, including propylene glycol in the water phase, as is known in the cosmetic arts, may provide additional humectant properties. Other water-soluble humectants may be substituted in corresponding amounts by weight, such as glycerin, sorbitol, etc.

The present invention and the results which can be obtained thereby are further illustrated by the following examples.

EXAMPLE I

A skin lotion comprising an oil-in-water emulsion is prepared according to Formula A as set out below:

| Formula A | |
|---|---|
| Ingredients | Weight % |
| Emollient oils and emulsifier | 13.5 |
| Cetyl alcohol (4.0%) | |
| Mineral oil (4.0%) | |
| Isopropyl myristate (3.0%) | |
| Dimethicone (1.0%) | |
| Lanolin alcohol (0.5%) | |
| Glyceryl monostearate (1.0%)[7] | |
| Quaternary ammonium cellulose ether polymer[1] | 0.3 |
| Sodium lactate (60% aq. sdu.) | 1.4 |
| Dimethyl di-(hydrogenated tallow) ammonium chloride (75% active)[2] | 2.0 |
| Propylene glycol[3] | 3.0 |
| Preservatives (0.2% methyl paraben and 0.1% propyl paraben)[4] | 0.3 |
| Titanium dioxide[5] | 0.1 |
| Perfume | 0.1 |
| Water[6] | 79.3 |
| | 100.0 |

[1]Polymer JR 400, approx. mol. wt. 400,000, Union Carbide Corp., New York, N.Y.
[2]Arquad 2HT75, Armak Chemical Co., McCook, Illinois.
[3]Optional humectant-emollient in aqueous phase.
[4]Methyl paraben in aqueous phase and propyl paraben in oil phase.
[5]Whitener.
[6]pH of aqueous phase of complete composition is preferably 5.5 to 5.6
[7]Glycerol monostearate acts as an oil-in-water emulsifier.

The procedure used for combining the foregoing ingredients is as follows: Deionized water is metered into a mixing tank (Tank A), withholding 20 gallons. Propylene Glycol is added and solution is heated to 160°–165° F. Propyl paraben is added under high sheer agitation for 30 minutes and is completely dissolved before continuing. 160°–165° F. is maintained. With vigorous agitation, the quaternary ammonium cellulose ether polymer is slowly added to Tank A and mixed for 60 minutes. The solution must be completely free of lumps before continuing. In an oil phase mixing tank (Tank B) add the emollient oils, emulsifier, prewarmed dimethyl di-(hydrogenated tallow) ammonium chloride (75% active), and propyl paraben. Heat and maintain 160°–165° F. with moderate agitation for 30 minutes. While maintaining the temperature of both the water phase and oil phase at 155°–165° F., pump the water phase (Tank A) into the oil phase (Tank B) and agitate moderately. Rinse Tank A with 20 gallons of 160°–165° F. deionized water and add to Tank B. Add the titanium dioxide and mix for 60 minutes. Cool batch slowly to 130° F. Add the sodium lactate (60%) to the batch.

12. Repeat steps 6 through 11 twice.
13. Calculate the amount of polymer substantive to the skin and report the median value.
14. Repeat steps 4 through 13 for a five minute immersion.

The data obtained is summarized below in Table A.

TABLE A

| Preparation | Constant | | Variable | | % Substantivity of Polymer JR 400 | |
|---|---|---|---|---|---|---|
| | | | | | 1 min. | 5 min. |
| 1 | Polymer JR-400 | 0.3% | Sodium Lactate | 0% | 77 | 50 |
| | Emollient oil | 13.5% | Arquad 2HT75 | 0% | | |
| 2 | Polymer JR-400 | 0.3% | Sodium Lactate | 1.5% | 73 | 61 |
| | Emollient oil | 13.5% | Arquad 2HT75 | 0% | | |
| 3 | Polymer JR-400 | 0.3% | Sodium Lactate | 1.5% | 86 | 68 |
| | Emollient oil | 13.5% | Arquad 2HT75 | 2.0% | | |
| 4 | Polymer JR-400 | 0.3% | Sodium Lactate | 0% | 93 | 26 |
| | Emollient oil | 13.5% | Arquad 2HT75 | 2.0% | | |

Continue to cool slowly with agitation. Cool batch to 100° F. Add the perfume and continue mixing for 60 minutes.

EXAMPLE II

Oil-in-water emulsions prepared as described in Example I and containing Polymer JR 400 was studied to determine the effect of the sodium lactate and/or the Arquad 2HT75 on the substantivity of the Polymer JR. In Preparation 1 both sodium lactate and Arquad 2HT75 were omitted, in Preparation 2, sodium lactate was included at 1.5%, in Preparation 3, sodium lactate was included at 1.5% together with Arquad 2HT75 at 2.0%, and in Preparation 4, sodium lactate was omitted and Arquad 2HT75 was included at 2.0%. In all preparations, the mixture of emollient oil was kept constant at 13.5%. In these preparations, Carbon 14-tagged Polymer JR 400 was used to permit the substantivity to be determined by measurement of radio activity. In the comparative tests, a Neo-natal rat skin procedure was used as follows:

NEO-NATAL RAT SKIN PROCEDURE

1. Cut a neo-natal rat skin (*stratum corneum*) into three equal pieces. Each skin is approximately 40 mm square.
2. Pipette ten microliters of lotion on each piece using a microsyringe.
3. Insert the coated piece into a counting vial and dissolve with the appropriate tissue solubilizer, add 20 ml. of the compliment and count via liquid scintillation techniques at 40° F. The amount of radio activity obtained for these samples serves as the control for the experiment.
4. Cut a neo-natal rat skin into three pieces.
5. Pipette ten microliters of lotion on each piece using a microsyringe.
6. Work the lotion into the skin. Then allow it to stand for 90 minutes.
7. Immerse one piece into a 0.5% solution of LUX Dishpan Detergent (sodium lauryl sulfate) heated to 40° C.
8. Remove the skin after one minute and insert it into a counting vial.
9. Dissolve the skin and lotion with the appropriate tissue solubilizer.
10. Add 20 ml. of compliment.
11. Count via the liquid scintillation technique at 40° F.

Statistical analysis of the foregoing data shows that the sodium lactate when used alone significantly increased the substantivity of the Polymer JR after five minutes of contact with the detergent solution. On the other hand, where the Arquad 2HT75 was used alone with the Polymer JR, the retention of the Polymer JR was significantly decreased after five minutes. Further, where both sodium lactate and Arquad 2HT75 are present, there is a synergistic improvement in the substantivity of the Polymer JR both initially and after five minutes.

The foregoing data and conclusions indicated that the preparations of the present invention can be advantageously used for pretreatment of skin prior to exposure to anionic synthetic detergents and soaps. The lotion is applied to the area of the skin which will come in contact with the detergents or soaps, such as the hands prior to dishwashing, or the face prior to shampooing of hair. The lotion is applied liberally and rubbed into the skin. In addition, the preparations may be advantageously used as a general protective lotion for all areas of the body.

I claim:

1. A protective skin lotion composition in the form of an oil-in-water emulsion, the dispersed oil phase comprising an admixture of cosmetic emollient oils and forming from 5 to 35% by weight of said composition, the continuous water phase comprising from 95 to 65% by weight of said composition containing quaternary ammonium cellulose ether polymer in the amount of 0.05 to 3.0% based on the weight of said composition, wherein the improvement comprises increasing the skin retention of the cellulose polymer by also incorporating in said water phase from 0.3 to 3.0% of lactate salt based on the weight of said composition, said lactate salt being selected from the class consisting of sodium lactate, potassium lactate, and ammonium lactate, the pH of said water phase being in the range from 5.0 to 6.0, and incorporating in the oil phase from 0.5 to 4.0% of an oil-soluble quaternary ammonium salt based on the weight of said composition, said quaternary salt being selected from the class consisting of the chloride salt of a dimethyl di-aliphatic quaternary and the sulfate salt of a dimethyl di-aliphatic quaternary in which the aliphatic groups contain from 12 to 18 carbons.

2. The liquid composition of claim 1 in which said quaternary ammonium salt is a dimethyl di-aliphatic quaternary in which said aliphatic groups are composed predominantly of stearyl and palmityl groups.

3. A protective skin lotion composition in the form of an oil-in-water emulsion, the dispersed oil phase comprising an admixture of cosmetic emollient oils and forming from 8 to 20% by weight of said composition, the continuous water phase comprising from 95 to 65% by weight of said composition containing quaternary ammonium cellulose ether polymer in the amount of 0.1 to 0.5% based on the weight of said composition, wherein the improvement comprises increasing the skin retention of the cellulose polymer by incorporating in said water phase from 0.5 to 1.5% of lactate salt based on the weight of said composition, said lactate salt being selected from the class consisting of sodium lactate, potassium lactate, and ammonium lactate, and incorporating in the oil phase from 1.0 to 3.0% of a quaternary ammonium salt based on the weight of said composition, said quaternary ammonium salt being selected from the class consisting of the chloride salt of a dimethyl di-aliphatic quaternary, and the sulfate salt of a dimethyl di-aliphatic quaternary in which the aliphatic groups contain from 12 to 18 carbons, the pH of said water phase being in the range from 5.0 to 6.0.

4. The liquid composition of claim 3 in which the aliphatic groups of said quaternary ammonium salt are composed predominantly of stearyl and palmityl groups.

5. The liquid composition of claim 1 or claim 3 in which said lactate salt is sodium lactate and in which said quaternary ammonium salt is dimethyl di-(hydrogenated tallow) quaternary ammonium chloride.

* * * * *